United States Patent
Chang et al.

(10) Patent No.: US 10,787,409 B1
(45) Date of Patent: Sep. 29, 2020

(54) METHOD FOR PRODUCING CYCLOHEXANONE DIMER

(71) Applicant: CHINA PETROCHEMICAL DEVELOPMENT CORPORATION, TAIPEI (TAIWAN), Kaohsiung (TW)

(72) Inventors: Chih-Cheng Chang, Kaohsiung (TW); Hong-Kai Yang, Kaohsiung (TW); Chia-Tsen Tsai, Kaohsiung (TW); Chia-Hui Shen, Kaohsiung (TW)

(73) Assignee: CHINA PETROCHEMICAL DEVELOPMENT CORPORATION, TAIPEI (TAIWAN), Kaohsiung (TW)

( * ) Notice: Subject to any disclaimer, the term of this patent is extended or adjusted under 35 U.S.C. 154(b) by 0 days.

(21) Appl. No.: 16/843,037

(22) Filed: Apr. 8, 2020

(30) Foreign Application Priority Data

Sep. 3, 2019 (TW) .................................. 108131693

(51) Int. Cl.
*C07C 45/68* (2006.01)
(52) U.S. Cl.
CPC .................................... *C07C 45/68* (2013.01)
(58) Field of Classification Search
CPC .................................................... C07C 45/68
See application file for complete search history.

(56) References Cited

U.S. PATENT DOCUMENTS

| | | | | |
|---|---|---|---|---|
| 3,880,930 A * | 4/1975 | Ramm | .................... | C07C 45/74 568/352 |
| 3,980,716 A * | 9/1976 | Elliott | ..................... | C07C 37/07 568/747 |
| 4,002,693 A * | 1/1977 | King | ....................... | C07C 37/07 568/747 |
| 4,088,702 A * | 5/1978 | Goto | ....................... | C07C 37/06 502/223 |
| 8,519,192 B2 * | 8/2013 | Ma | ......................... | B01J 27/053 568/338 |

OTHER PUBLICATIONS

Deng et al. Highly selective self-condensation of cyclic ketones using MOF-encapsulating phosphotungstic acid for renewable high-density fuel. Green Chemistry, vol. 17, 4473-4481. (Year: 2015).*

* cited by examiner

*Primary Examiner* — Sikarl A Witherspoon
(74) *Attorney, Agent, or Firm* — Hoxie & Associates LLC

(57) ABSTRACT

A method for producing a cyclohexanone dimer is provided. The method includes the steps of performing condensation of cyclohexanone in the presence of a solid acid catalyst to obtain the cyclohexanone dimer, wherein the solid acid catalyst includes metal oxide of tungsten and a carrier with Lewis acid sites and Brønsted acid sites. The method of the present disclosure has an advantage of mild reaction condition, fast reaction rate and high selectivity, thereby realizing the value of the industrial application.

18 Claims, 1 Drawing Sheet

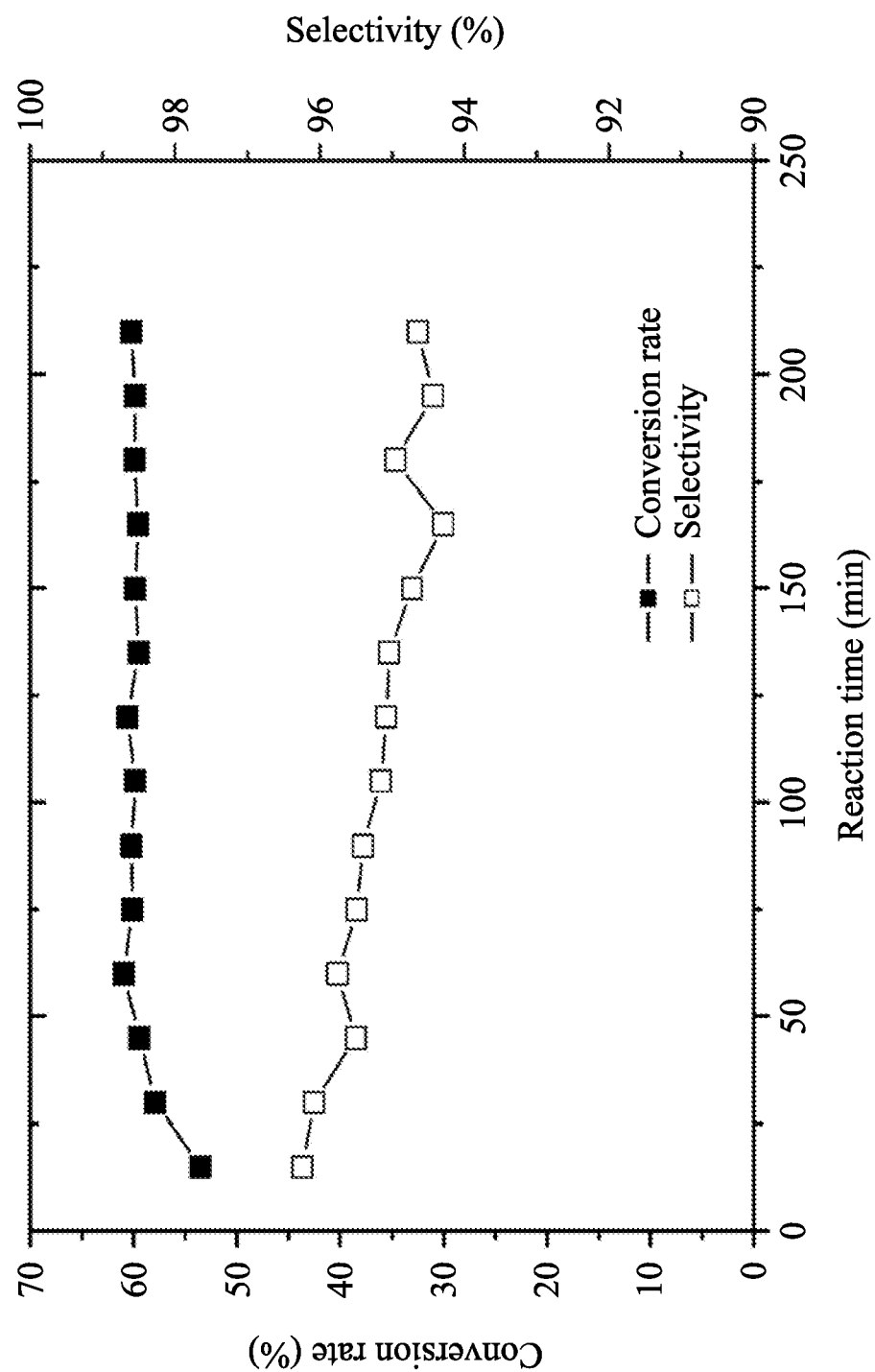

METHOD FOR PRODUCING CYCLOHEXANONE DIMER

CROSS-REFERENCE TO RELATED APPLICATIONS

This application is a U.S. non-provisional application filed under 35 U.S.C. § 111(a) which claims priority to, and the benefit of, Taiwanese Patent Application No. 108131293, filed on Sep. 3, 2019, the contents of which are hereby incorporated by reference in its entirety.

BACKGROUND

1. Technical Field

The present disclosure relates to methods for producing cyclohexanone dimers, and more particularly, to a method for producing a cyclohexanone dimer in the presence of a solid acid catalyst.

2. Description of Related Art

Cyclohexanone is an important product of chemical engineering, which can be used currently as an intermediate material in synthesis of o-phenylphenol, in addition to being a modifier for epoxy resins, an herbicide, an insecticide, a plasticizer for plastics, a preservative for woods and a cross-linking agent for polymers. O-phenylphenol, which is broadly used in the fields of microbicides, textile auxiliaries, surfactants, fire retardants, preservatives, plastic stabilizers, novel synthetic plastics, or resins, is an important organic fine chemical product.

Currently, the methods for producing a cyclohexanone dimer generally utilize cyclohexanone as the raw material and perform intermolecular condensation of cyclohexanone in the presence of an acid or a base, wherein the condensation of cyclohexanone is a nucleophilic substitution taking place on the α-carbon atom with the reaction scheme in the following:

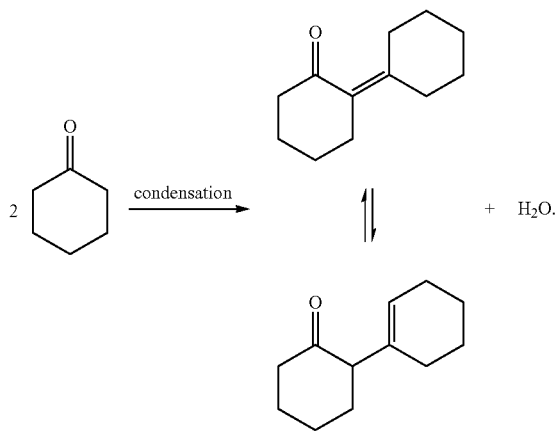 [SMILES: O=C1CCCCC1 ; O=C1CCCCC1=C1CCCCC1 ; "H2O." ; O=C1CCCCC1C1=CCCCC1]

The thus-obtained product includes two tautomers, namely 2-(1-cyclohexenyl)cyclohexanone and 2-(cyclohexylidene)cyclohexanone, respectively.

A base catalyst commonly used in production of a cyclohexanone dimer is calcium hydroxide, which has the disadvantages of poor reaction effects after regeneration of the catalyst, a high reaction temperature, a poor selectivity of the product, and a potential problem of corrosion to the apparatus.

An acid catalyst commonly used in production of cyclohexanone dimer can be an organic acid or an inorganic acid. However, an organic acid or an inorganic acid causes severe corrosion to production apparatus, and a complex purification process is required as the catalyst would be remained in the product, resulting in problems of increased production cost and environmental pollution. Although there have been studies on the use of solid acid catalysts, such techniques still have the disadvantages of low selectivity and many byproducts.

In addition, in order to remove water generated from the reaction in time, a water-removing agent, such as, cyclohexane, n-heptane, benzene, and the like, would be used in the existing processes to facilitate the reaction and to avoid byproduct formation due to high temperatures, which would otherwise result in reduced selectivity of the cyclohexanone dimer. However, the use of a water-removing agent needs to arrange a distillation apparatus at the later stage of the process for removing it, resulting in an increased cost for production.

In view of the foregoing, it is necessary to propose a method for producing a cyclohexanone dimer with a low cost and a high selectivity to solve the problems existing in the conventional techniques described above.

SUMMARY

In order to solve the problems described above, the present disclosure provides a method for producing a cyclohexanone dimer, which comprises: performing condensation of cyclohexanone in the presence of a solid acid catalyst to produce a cyclohexanone dimer, wherein the solid acid catalyst comprises metal oxide of tungsten and a carrier with Lewis acid sites and Brønsted acid sites.

In an embodiment of the present disclosure, the method for preparing a solid acid catalyst comprises subjecting a tungsten salt precursor and the carrier to rotary calcination at a temperature of from 300 to 600° C. to obtain the solid acid catalyst.

In an embodiment of the present disclosure, the carrier is zeolite with a specific surface area of from 600 to 700 m$^2$/g.

In another embodiment of the present disclosure, the zeolite can be in at least one form selected from the group consisting of Y-type, β-type and ZSM-5 type zeolites.

In an embodiment of the present disclosure, the metal oxide of tungsten is tungsten trioxide, and in an embodiment, the tungsten trioxide is loaded on the carrier in an amount of from 0.5 wt % to 6.0 wt %.

In an embodiment of the present disclosure, the solid acid catalyst further comprises a second metal oxide, of which a metal is at least one selected from the group consisting of alkaline earth metals, scandium, titanium, vanadium, chromium, manganese, iron, cobalt, nickel, copper and zinc, and in an embodiment, the second metal oxide is loaded on the carrier in an amount of from 0.1 wt % to 3.0 wt %.

In an embodiment of the present disclosure, the second metal oxide covers the Lewis acid sites of the carrier. For example, the second metal oxide is titanium dioxide.

In still another embodiment of the present disclosure, the second metal oxide covers the Brønsted acid sites of the carrier. For example, the second metal oxide is magnesium oxide.

In an embodiment of the present disclosure, condensation of cyclohexanone is performed at a temperature of from 120 to 220° C.

In an embodiment of the present disclosure, the method can be carried out in a batch reactor, and condensation of cyclohexanone is performed for 0.25 to 1 hr, wherein the weight ratio of the solid acid catalyst to cyclohexanone is from 0.01 to 0.05.

In an embodiment of the present disclosure, the method can be carried out in a continuous reactor with a water removal unit, and cyclohexanone is remained in the reactor for 0.25 to 3 hr. In an embodiment, the weight hourly space velocity of cyclohexanone is from 1 to 10 $hr^{-1}$.

In the method of the present disclosure, a catalyst containing metal oxide of tungsten and having Lewis acid sites and Brønsted acid sites is used, and the rate and selectivity of reaction are enhanced under relative milder conditions. Further, with the method of the present disclosure, the problem of byproduct formation due to high temperature and the use of water-removing agent or other solvent are avoided to simplify the separation and purification processes at a later stage of the method and to reduce the cost of raw materials and processing, such that the value of industrial application is realized.

BRIEF DESCRIPTION OF THE DRAWINGS

The implementation modes of the present disclosure will be described by reference to the appended drawing:

FIG. 1 is a graph showing changes in conversion rate and selectivity over reaction time in Example 4-4 of the present disclosure.

DETAILED DESCRIPTION OF THE EMBODIMENTS

The implementation modes of the present disclosure are illustrated by following specific embodiments, any one skilled in the art can easily conceive the advantages and effects of the present disclosure based on the content of the present specification. The present disclosure also can be performed or applied by other different implementation modes, and the details of the present disclosure each can be imparted with different modifications and alternations based on different views and applications without departing from the spirit of the present disclosure. Furthermore, all of the ranges and values recited in the present disclosure are inclusive and combinable. Any value or point fallen within the ranges recited herein, such as any integers, can be used as the lower or upper limit to derive a subrange.

The method of the present disclosure for producing a cyclohexanone dimer comprises: performing condensation of cyclohexanone in the presence of a solid acid catalyst to produce a cyclohexanone dimer, wherein the solid acid catalyst comprises metal oxide of tungsten and a carrier for bearing the metal oxide of tungsten, wherein the carrier has Lewis acid sites and Brønsted acid sites.

The condensation of cyclohexanone is the intermolecular dehydration of cyclohexanone in the presence of a solid acid catalyst to form a cyclohexanone dimer. The cyclohexanone dimer includes two tautomers, i.e., 2-(1-cyclohexenyl)cyclohexanone and 2-(cyclohexylene)cyclohexanone, with 2-(1-cyclohexenyl)cyclohexanone being the main component.

In an embodiment, the condensation of cyclohexanone is performed at a temperature of from 120 to 220° C. It is adverse to progress of the reaction catalyzed by a solid acid catalyst of the present disclosure, if the condensation temperature is too low; and a side reaction tends to occur, if the condensation temperature is too high. In some embodiments, the condensation reaction of cyclohexanone can be performed at 120, 125, 130, 135, 140, 145, 150, 155, 160, 165, 170, 175, 180, 185, 190, 195, 200, 205, 210, 215, or 220° C.

The solid acid catalyst of the present disclosure employs metal oxide of tungsten as the active ingredient to facilitate acceleration of the reaction and improvement of productivity by increasing acid sites of the catalyst with metal oxide of tungsten.

In an embodiment, tungsten trioxide as metal oxide of tungsten is preferable, since tungsten trioxide is in a higher oxidation state and therefore can increase acidity of the catalyst efficiently. More specifically, tungsten trioxide is loaded on the carrier in an amount of from 0.5 wt % to 6.0 wt %, and in some embodiments, tungsten trioxide is loaded on the carrier in an amount of 0.5, 1.0, 2.5, 2.0, 2.5, 3.0, 3.5, 4.0, 4.5, 5.0, 5.5, or 6.0 wt %.

In the present disclosure, "the amount of tungsten trioxide loaded" refers to the content of tungsten trioxide that the carrier bears, i.e., the weight ratio of tungsten trioxide to the carrier.

The conversion rate of reaction would be too low if the amount of tungsten trioxide loaded is less than 0.5 wt %; and the conversion rate of reaction cannot be further enhanced while the production cost increases if the amount of tungsten trioxide loaded is more than 6 wt %, because the excessive tungsten trioxide would overlap and block active sites thereof to reduce the surface area in contact with reactants.

The solid acid catalyst can be regenerated and recycled. In an embodiment, the solid acid catalyst is regenerated by burning.

The solid acid catalyst is obtained by mixing, immersing, drying for water removal, and calcining in sequence. In an embodiment, the preparation process of the solid acid catalyst comprises subjecting a tungsten salt precursor and a carrier to rotary calcination at a temperature of from 300 to 600° C. to obtain the solid acid catalyst. In some embodiments, the temperature is 300, 350, 400, 450, 500, 550, or 600° C.

For example, the preparation of the solid acid catalyst includes: dissolving a tungsten salt precursor in a solvent, immersing a porous carrier in the dissolved tungsten salt precursor to form a mixture, allowing the porous carrier to adsorb the tungsten salt precursor on the surface or in the pores, then, removing water from the mixture such as by drying the mixture to remove water through a rotary evaporator, and finally, subjecting the tungsten salt precursor and the carrier to a rotary calciner at a temperature of from 300 to 600° C. for 6 to 10 hrs to obtain the solid acid catalyst.

In an embodiment, the tungsten salt precursor is a compound with a tungsten content of from 0.5 wt % to 6 wt %. For example, the tungsten salt precursor can be selected from ammonium metatungstate hydrate $((NH_4)_6H_2W_{12}O_{40} \cdot xH_2O$, wherein x is an integer of from 1 to 4) or ammonium tungstate $((NH_4)_{10}W_{12}O_{41})$. In some embodiments, the tungsten salt precursor is a compound with a tungsten content of 0.5, 1.0, 2.5, 2.0, 2.5, 3.0, 3.5, 4.0, 4.5, 5.0, 5.5, or 6.0 wt %.

The carrier has the function of bearing metal oxide of tungsten to disperse metal oxide of tungsten, thereby increasing the catalytic activity. In addition, the carrier has Lewis acid sites and Brønsted acid sites, i.e., the surface of the carrier has capabilities for receiving electrons and donating protons at the same time, therefore, the acid strength and catalytic activity of the solid acid catalyst are increased, and the effects of improved reaction selectivity and accelerated reaction are increased.

In an embodiment, the carrier can be selected from materials having a plurality of porous structures or channel structures, for example, modified or unmodified montmorillonite or zeolite can be used without any restriction on its form.

In an embodiment, the carrier is zeolite, wherein the zeolite carrier has a specific surface area of from 600 to 700 $m^2/g$.

In some embodiments, the zeolite carrier can have a specific surface area of 600, 610, 620, 630, 640, 650, 660, 670, 680, 690, or 700 $m^2/g$, but not limited thereto.

The zeolite has a crystal structure of aluminosilicate with its charge distribution altered in different crystal structural arrangements. Thus, different packing modes result in different catalytic activities. In an embodiment, the zeolite can be in at least one form selected from the group consisting of Y-type, β-type and ZSM-5 type zeolites, among which the Y-type and β-type zeolites are preferable.

In another embodiment, the solid acid catalyst can further include a second metal oxide, and therefore, less poisoning phenomena of the active ingredients would occur to prolonged service time and improved conversion rate of the reaction by using the mixed loading of the second metal oxide and metal oxide of tungsten.

The metal in the second metal oxide is at least one selected from the group consisting of alkaline earth metals, scandium, titanium, vanadium, chromium, manganese, iron, cobalt, nickel, copper and zinc. In addition, the second metal oxide is loaded in an amount of from 0.1 wt % to 3.0 wt %. In some embodiments, the second metal oxide is loaded in an amount of 0.1, 0.2, 0.3, 0.4, 0.5, 0.6, 0.7, 0.8, 0.9, 1.0, 1.5, 2.0, 2.5, or 3.0 wt %.

In the present disclosure, the "amount of the second metal oxide loaded" refers to the content of the second metal oxide loaded on the carrier bearing metal oxide of tungsten, i.e., the weight ratio of the second metal oxide to the total weight of metal oxide of tungsten and the carrier.

The method for preparing a solid acid catalyst with a mixture of metal oxide of tungsten and the second metal oxide loaded thereon further comprises, following the preparation of the solid acid catalyst containing the metal oxide of tungsten and the carrier, placing a second metal salt precursor and the solid acid catalyst containing metal oxide of tungsten and the carrier in a solvent to form a mixture; then removing water from the mixture, such as by drying the mixture through a rotary evaporator to remove water; and performing rotary calcination at a temperature of from 300 to 600° C. for 6 to 10 hrs, to give the solid acid catalyst with the mixture of metal oxide of tungsten and the second metal oxide loaded thereon.

In an embodiment, the second metal oxide covers the Lewis acid sites of the carrier. For example, the second metal oxide is titanium dioxide.

In another embodiment, the second metal oxide covers the Brønsted acid sites of the carrier. For example, the second metal oxide is magnesium oxide.

The method for producing a cyclohexanone dimer of the present disclosure can be applied with a batch process or a continuous process. However, the reactor used in the method for producing a cyclohexanone dimer of the present disclosure is free of a water-removing agent or other solvent such as cyclohexane, n-heptane or benzene, despite of whether the batch process or the continuous process is employed.

In a batch process, the reactor is a batch reactor operated in such a mode that the reactor is loaded in batches to perform the reaction and unloaded when the reaction is completed or performed for a predetermined period. In the Examples of the present disclosure, the batch reactor further includes an agitator device, which is a stirred tank reactor, and the agitator device rotates at a speed of from 150 to 300 rpm. The agitator device can be selected from a propeller-type agitator, a turbine agitator, a blade agitator, an anchor agitator, a folding blade agitator, a side agitator, a propeller agitator, a magnetic heating agitator, or a helical ribbon agitator.

In an embodiment, when the reactor is a batch reactor, the method comprises: mixing a solid acid catalyst with cyclohexanone at a weight ratio of the solid acid catalyst to cyclohexanone of from 0.01 to 0.05, such as, 0.01, 0.02, 0.03, 0.04, or 0.05; and performing condensation of cyclohexanone at a temperature ranging from 120 to 220° C. for 0.25 to 1 hrs.

In another embodiment, when the reactor is a batch reactor, the method further comprises: removing the solid acid catalyst by filtration after the condensation of cyclohexanone is completed, and performing a vacuum distillation treatment on the filtrate after filtration to recover unreacted cyclohexanone, thereby obtaining a cyclohexanone dimer product with high purity.

In a continuous process, the reactor is a continuous reactor operated by continuous feeding, continuous reaction and continuous unloading, wherein the continuous reactor comprises a water removal unit, and examples of the continuous reactor include a fixed bed reactor, a moving bed reactor, a fluidized bed reactor or a continuous stirring tank reactor.

In an embodiment, when the reactor is a continuous reactor having a water removal unit, the method comprises: packing a solid acid catalyst in the continuous reactor; feeding cyclohexanone into the continuous reactor; performing condensation of cyclohexanone at 120 to 220° C., while allowing cyclohexanone to be remained in the continuous reactor for 0.25 to 3 hrs, such as, for 0.25, 0.3, 0.35, 0.4, 0.45, 0.5, 0.55, 0.6, 0.65, 0.7, 0.75, 0.8, 0.85, 0.95, 1, 1.5, 2, 2.5, or 3 hrs; and discharging the product stream after reaction from the continuous reactor.

Since the continuous reactor of the present disclosure is a heterogeneous reaction system, the flow rate of the reactant steam can affect flow layer thickness thereof on the catalyst and the mass delivery between reactants. In an embodiment, the weight hourly space velocity of cyclohexanone is from 1 to 10 hr$^{-1}$, such as 1, 2, 3, 4, 5, 6, 7, 8, 9, or 10 hr$^{-1}$, when the condensation reaction of cyclohexanone is performed at 120 to 220° C. In some embodiments, the condensation reaction of cyclohexanone is performed at 120, 125, 130, 135, 140, 145, 150, 155, 160, 165, 170, 175, 180, 185, 190, 195, 200, 205, 210, 215, or 220° C.

In another embodiment, when the reactor is a continuous reactor with a water removal unit, the method further comprises: performing a vacuum distillation treatment on the product stream, and refluxing unreacted cyclohexanone to the continuous reactor, thereby obtaining a cyclohexanone dimer product with high purity and improving conversion rate of the reaction.

The features and effects of the present disclosure are described in detail through the following specific Examples, which should not be considered as limiting the scope of the present disclosure.

The selectivity disclosed in the specification is defined in the following:

$$\text{Selectivity} = 2 \times \frac{\text{moles of cyclohexanonedimer in the product}}{\text{moles of cyclohexanone consumed}} \times 100\%$$

Catalyst Preparation Example 1

Ammonium metatungstate ((NH$_4$)$_6$H$_2$W$_{12}$O$_{40}$·xH$_2$O, MDL number: MFCD00150662, available from Strem Chemicals, Inc.) with a tungsten content of 72 wt % (1.72 g) as the tungsten salt precursor was dissolved in deionized water (250 g) and placed in a 500 mL flask. Y-type zeolite (40 g) as a carrier for bearing metal oxide of tungsten was immersed in the solution of tungsten salt precursor to form a mixture, wherein the zeolite carrier had a specific surface area of 600 m$^2$/g.

Then, the mixture was uniformly dispersed and dried for water removal through a rotary evaporator at 80° C. The tungsten salt precursor and the carrier were calcined with the rotary evaporator at 450° C. for 6 hrs to obtain a WO$_3$/Y-type zeolite catalyst with 3 wt % WO$_3$ loaded thereon.

Catalyst Preparation Example 2

The preparation method described in Preparation Example 1 was used to obtain WO$_3$/Y-type zeolite catalyst with 0.5 wt % WO$_3$ loaded thereon, except that the addition amount of ammonium metatungstate was changed to be 0.28 g.

Catalyst Preparation Example 3

The preparation method described in Preparation Example 1 was used to obtain WO$_3$/ZSM-5 type zeolite catalyst with 3 wt % WO$_3$ loaded thereon, except that the carrier was changed to be ZSM-5 type zeolite.

Catalyst Preparation Example 4

The preparation method described in Preparation Example 1 was used to obtain WO$_3$/β-type zeolite catalyst with 0.5 wt % WO$_3$ loaded thereon, except that the addition amount of ammonium metatungstate was changed to be 0.28 g and β-type zeolite was used as the carrier.

Catalyst Preparation Example 5

The WO$_3$/Y-type zeolite catalyst of Preparation Example 1 (20 g), magnesium nitrate (0.13 g) as the second metal precursor, and deionized water (150 g) were charged into a 500 mL flask to form a mixture.

Then, the mixture was uniformly dispersed and dried for water removal through the rotary evaporator at 80° C. The tungsten salt precursor and the carrier were calcined with the rotary evaporator at 450° C. for 6 hrs to obtain a MgO.WO$_3$/Y-type zeolite catalyst with 0.1 wt % MgO and 3 wt % WO$_3$ loaded thereon.

Catalyst Preparation Example 6

The preparation method described in Preparation Example 5 was used to obtain a TiO$_2$.WO$_3$/Y-type zeolite catalyst with 0.1 wt % TiO$_2$ and 3 wt % WO$_3$ loaded thereon, except that tetraethyl titanate (0.1 g) and ethanol were used instead of magnesium nitrate (0.13 g) and deionized water, respectively, and the mixture was dispersed uniformly and dried to remove water from the rotary condenser at temperature of 60° C.

Example 1

Cyclohexanone (300 g) and the WO$_3$/Y-type zeolite catalyst (12 g) of Preparation Example 1 were charged into a 1 L batch reactor with an agitator, wherein the weight ratio of the solid acid catalyst to cyclohexanone was 0.04, and condensation of cyclohexanone was performed at a temperature of 180° C. for 1 hr to obtain a cyclohexanone dimer.

The product was analyzed using a water content analyzer and a gas chromatograph (GC), and the conversion rate and selectivity of the reaction are recorded in Table 1.

Examples 1-1 to 1-2

The preparation method described in Example 1 was used to obtain the cyclohexanone dimer product, except that the reaction temperature were changed as shown in Table 1, and the results including the conversion rates and selectivities are recorded in Table 1.

TABLE 1

| | Catalyst | | | Reaction conditions | | Reaction results | |
|---|---|---|---|---|---|---|---|
| | Active ingredient | Carrier | Active ingredient content (%) | Temperature (° C.) | Time (hrs) | Conversion rate (%) | Selectivity (%) |
| Ex. 1 | $WO_3$ | Y-type Zeolite | 3 | 180 | 1 | 63.9 | 95.5 |
| Ex. 1-1 | | | | 160 | | 52.8 | 97.3 |
| Ex. 1-2 | | | | 140 | | 38.4 | 98.2 |

Example 2

The preparation method described in Example 1 was used to obtain the cyclohexanone dimer product, except that a catalyst of $WO_3$/Y-type zeolite with a $WO_3$ loading amount of 0.5 wt % of Preparation Example 2 was used instead of the catalyst of $WO_3$/Y-type zeolite with a $WO_3$ loading amount of 3 wt % of Preparation Example 1, and the results including the conversion rates and selectivities are recorded in Table 2.

Example 3

The preparation method described in Example 1 was used to obtain the cyclohexanone dimer product, except that a catalyst of $WO_3$/ZSM-5 type zeolite of Preparation Example 3 was used instead of the catalyst of $WO_3$/Y-type zeolite of Preparation Example 1, and the results including the conversion rates and selectivities were recorded in Table 2.

Example 4

The preparation method described in Example 1 was used to obtain the cyclohexanone dimer product, except that a catalyst of $WO_3$/β-type zeolite of Preparation Example 4 was used instead of the catalyst of $WO_3$/Y-type zeolite of Preparation Example 1 and the reaction time was shorten to 0.25 hrs, and the results including the conversion rates and selectivities are recorded in Table 2.

TABLE 2

| | Catalyst | | | Reaction conditions | | Reaction results | |
|---|---|---|---|---|---|---|---|
| Ex. No. | Active ingredient | Form of the zeolite carrier | Active ingredient content (%) | Temperature (° C.) | Time (hrs) | Conversion rate (%) | Selectivity (%) |
| 1 | $WO_3$ | Y-type | 3 | 180 | 1 | 63.9 | 95.5 |
| 2 | | | 0.5 | | 1 | 56.3 | 96.7 |
| 3 | | ZSM-5 | 3 | | 1 | 32.0 | 98.8 |
| 4 | | β-type | 0.5 | | 0.25 | 66.0 | 94.0 |

Examples 4-1 to 4-3

The preparation method described in Example 4 was used to obtain the cyclohexanone dimer product, except that the reaction temperature were changed as shown in Table 3, and the results including the conversion rates and selectivities are recorded in Table 3.

TABLE 3

| | Catalyst | | | Reaction conditions | | Reaction results | |
|---|---|---|---|---|---|---|---|
| Ex. No. | Active ingredient | Carrier | Active ingredient content (%) | Temperature (° C.) | Time (hrs) | Conversion rate (%) | Selectivity (%) |
| 4 | $WO_3$ | β-type Zeolite | 0.5 | 180 | 0.25 | 66.0 | 94.0 |
| 4-1 | | | | 160 | | 58.3 | 98.2 |
| 4-2 | | | | 150 | | 57.3 | 98.4 |
| 4-3 | | | | 140 | | 47.9 | 99.2 |

Example 4-4

The preparation method described in Example 4-2 was used to obtain the cyclohexanone dimer product, except that the reactor was changed to be a continuous reactor having a water removal unit, sampling was done during reaction every 0.25 hrs, and the results including the conversion rates and selectivities are recorded in FIG. 1.

Example 5

The preparation method described in Example 1 was to obtain the cyclohexanone dimer product, except that a catalyst of $MgO \cdot WO_3$/Y-type zeolite of Preparation Example 5 was used instead of the catalyst of $WO_3$/Y-type zeolite of Preparation Example 1, and the results including the conversion rates and selectivities are recorded in Table 4.

Example 6

The preparation method described in Example 1 was used to obtain the cyclohexanone dimer product, except that a catalyst of $TiO_2 \cdot WO_3$/Y-type zeolite of Preparation Example 6 was used instead of the catalyst of $WO_3$/Y-type zeolite of Preparation Example 1, and the results including the conversion rates and selectivities are recorded in Table 4.

TABLE 4

| | Catalyst | | Reaction conditions | | Reaction results | |
|---|---|---|---|---|---|---|
| First active ingredient and content thereof | Second active ingredient and content thereof | Carrier | Temperature (° C.) | Time (hrs) | Conversion rate (%) | Selectivity (%) |
| Ex. 1 | 3% $WO_3$ | — | Y-type Zeolite | 180 | 1 | 63.9 | 95.5 |
| Ex. 5 | | 0.1% MgO | | | | 41.4 | 98.9 |
| Ex. 6 | | 0.1% TiO2 | | | | 61.1 | 96.1 |

In conclusion, the method of present disclosure for producing a cyclohexanone dimer utilizes a catalyst containing metal oxide of tungsten and having Lewis acid sites and Brønsted acid sites, and enhances the rate and selectivity of reaction under mild conditions. Further, with the method of the present disclosure, the problem of byproduct formation due to high temperatures and the use of water-removing agent or other solvent are avoided to simplify the separation and purification processes at the later stage of the method and to reduce the cost of raw materials and the process, and therefore, the value of industrial application are realized.

The above Examples are used for illustration only, and not for limiting the present disclosure. Modifications and alternations can be made to above Examples by any one skilled in the art without departing from the spirit and scope of the present disclosure. Therefore, the scope of the present application is defined by the appended claims, and should be encompassed within present disclosure as long as that doesn't influence effects and purposes of the present disclosure.

What is claimed is:

1. A method for producing a cyclohexanone dimer, comprising:
    performing condensation of cyclohexanone in the presence of a solid acid catalyst to obtain the cyclohexanone dimer,
    wherein the solid acid catalyst comprises metal oxide of tungsten and a carrier with Lewis acid sites and Brønsted acid sites.

2. The method of claim 1, further comprising subjecting a tungsten salt precursor and the carrier to rotary calcination at a temperature of from 300° C. to 600° C. to obtain the solid acid catalyst.

3. The method of claim 1, wherein the carrier is zeolite.

4. The method of claim 3, wherein the zeolite has a specific surface area of from 600 $m^2$/g to 700 $m^2$/g.

5. The method of claim 3, wherein the zeolite is in at least one form selected from the group consisting of Y-type, β-type and ZSM-5 type zeolite.

6. The method of claim 1, wherein the metal oxide of tungsten is tungsten trioxide.

7. The method of claim 6, wherein the tungsten trioxide is loaded on the carrier in an amount of from 0.5 wt % to 6.0 wt %.

8. The method of claim 1, wherein the solid acid catalyst further comprises a second metal oxide with a metal being at least one selected from the group consisting of alkaline earth metals, scandium, titanium, vanadium, chromium, manganese, iron, cobalt, nickel, copper and zinc.

9. The method of claim 8, wherein the second metal oxide is loaded on the carrier in an amount of 0.1 wt % to 3.0 wt %.

10. The method of claim 8, wherein the second metal oxide covers the Lewis acid sites of the carrier.

11. The method of claim 10, wherein the second metal oxide is titanium dioxide.

12. The method of claim 8, wherein the second metal oxide covers the Brønsted acid site of the carrier.

13. The method of claim 12, wherein the second metal oxide is magnesium oxide.

14. The method of claim 1, wherein the condensation is performed at a temperature of from 120° C. to 220° C.

15. The method of claim 14, wherein the condensation is carried out in a batch reactor for 0.25 hr to 1 hr.

16. The method of claim 15, wherein a weight ratio of the solid acid catalyst to the cyclohexanone is from 0.01 to 0.05.

17. The method of claim 14, wherein the condensation is carried out in a continuous reactor comprising a water-removing unit, and the residence time of the cyclohexanone is from 0.25 hr to 3 hr.

18. The method of claim 17, wherein the weight hourly space velocity of the cyclohexanone is from 1 $hr^{-1}$ to 10 $hr^{-1}$.

\* \* \* \* \*